United States Patent
Righini et al.

(10) Patent No.: US 11,406,957 B2
(45) Date of Patent: Aug. 9, 2022

(54) DNA BRIDGE METHODS FOR CAPTURING DNA MOLECULES

(71) Applicant: CENTRILLION TECHNOLOGY HOLDINGS CORPORATION, Grand Cayman (KY)

(72) Inventors: Maurizio Righini, Palo Alto, CA (US); Wei Zhou, Saratoga, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 61 days.

(21) Appl. No.: 16/978,044

(22) PCT Filed: Apr. 12, 2019

(86) PCT No.: PCT/US2019/027234
§ 371 (c)(1),
(2) Date: Sep. 3, 2020

(87) PCT Pub. No.: WO2019/200265
PCT Pub. Date: Oct. 17, 2019

(65) Prior Publication Data
US 2021/0016241 A1    Jan. 21, 2021

Related U.S. Application Data

(60) Provisional application No. 62/657,732, filed on Apr. 14, 2018.

(51) Int. Cl.
*B01J 19/00* (2006.01)
*C40B 40/06* (2006.01)
*C40B 50/18* (2006.01)

(52) U.S. Cl.
CPC .......... *B01J 19/0046* (2013.01); *C40B 40/06* (2013.01); *C40B 50/18* (2013.01); *B01J 2219/00596* (2013.01); *B01J 2219/00722* (2013.01)

(58) Field of Classification Search
CPC .......... B01J 19/0046; B01J 2219/00596; B01J 2219/00722; C40B 40/06; C40B 50/18;
(Continued)

(56) References Cited

U.S. PATENT DOCUMENTS

2012/0316086 A1    12/2012 Lin et al.
2014/0194324 A1    7/2014 Gormley et al.

OTHER PUBLICATIONS

Yang et al. Journal of Vacuum Science & Technology B: Microelectronics and Nanometer Structures Processing, Measurement, and Phenomena 25, 2352-2356 (2007) (Year: 2007).*
(Continued)

*Primary Examiner* — Jeremy C Flinders
*Assistant Examiner* — Taryn Kimberly Wood
(74) *Attorney, Agent, or Firm* — Wilson Sonsini Goodrich & Rosati

(57) ABSTRACT

The present disclosure relates to processes for suspending stretched nucleic acids over surface features. These processes can be used to prepare stretched nucleic acids that are more active in enzymatic reactions and other reactions than those laid down on a flat surface. These processes can be achieved by using a photoresist layer on top of a substrate, stretch a nucleic acid on top of the surface, and then remove part of the photoresist to form surface features that suspend the stretched nucleic acid. Furthermore, the formation of a hydrogel layer over the stretched nucleic acid and the surface features can transfer the stretched nucleic acid to the hydrogel for further reactions, including enzymatic reactions.

20 Claims, 13 Drawing Sheets

(58) Field of Classification Search
CPC ............ C12Q 1/6806; C12Q 2523/303; C12Q 2523/313; C12Q 2565/518; C12Q 2565/601; B05D 3/00; B05D 3/06
See application file for complete search history.

(56) References Cited

OTHER PUBLICATIONS

Duan et al. Biomicrofluidics 7, 026501 (2013) (Year: 2013).*
Reihn et al. PNAS Jul. 19, 2005 102 (29) 10012-10016 (Year: 2005).*
International Search Report and Written Opinion for corresponding PCT/US2019/27234 dated Aug. 16, 2019.

* cited by examiner

DNA BRIDGE METHODS FOR CAPTURING DNA MOLECULES

CROSS-REFERENCE

This application claims the benefit of U.S. Provisional Patent Application No. 62/657,732, filed Apr. 14, 2018, which application is entirely incorporated herein by reference.

BACKGROUND

Genetic information in organisms is contained in polymeric molecules known as nucleic acids such as deoxyribonucleic acid (DNA) and ribonucleic acid (RNA). A genome is the genetic material in a cell's chromosomes. DNA sequence information of a genome can be used to determine characteristics of an individual as well as the presence of or susceptibility to many common diseases, such as cancer and some metabolic disease. Further, knowledge of an individual's genome may provide an opportunity to personalize medical treatments since certain drugs may be more effective in individuals having a certain genetic makeup. Tools are developed to allow for faster and or more reliable sequence determination. In addition, molecular detection platforms, such as DNA microarrays, that are miniaturized and can be manufactured in high volumes may provide access to affordable disease detection to more people.

DNA microarrays have seen extensive use in a range of applications for genomic sequence analysis, including the detection and analysis of mutations and polymorphisms (SNP genotyping), cytogenetics (copy number), nuclear proteomics, gene expression profiling, and transcriptome analysis. While many of these applications can employ direct hybridization-based methodologies for readout, the use of enzymatic readout may offer certain distinct advantages. For example, there may be much higher level of discrimination afforded by polymerase extension or ligation of the arrayed sequences, compared with detection by hybridization alone.

SUMMARY

It can be desirable to stretch a nucleic acid on top of a surface and make the stretched nucleic acid enzymatically active. This disclosure presents a solution to the problems of current methods of stretching nucleic acids: after placing the stretched nucleic acid on a surface, some enzymatic reactions may not be performed on the stretched substrate, or some enzymatic reactions may perform less effectively when compared with nucleic acid suspended in a solution.

In one aspect, the present disclosure provides a method of processing at least one nucleic acid molecule on a surface of a substrate, comprising: (a) stretching a nucleic acid molecule on the surface of the substrate; and (b) forming a plurality of discrete features on the surface of the substrate by removing a plurality of subsections from the surface of the substrate; wherein the nucleic acid molecule is in contact with two members of the plurality of discrete features, thereby suspending a portion of the nucleic acid between the two members of the plurality of discrete features.

In some embodiments of aspects provided herein, the plurality of discrete features form a topographical pattern. In some embodiments of aspects provided herein, the nucleic acid molecule is in contact with two additional members of the plurality of discrete features. In some embodiments of aspects provided herein, an additional portion of the nucleic acid molecule is suspended between the two additional members of the plurality of discrete features. In some embodiments of aspects provided herein, the method further comprises: (c) forming a hydrogel on the surface of the substrate, the hydrogel being in contact with some or all members of the plurality of discrete features. In some embodiments of aspects provided herein, in (c) at least portions of the nucleic acid molecule are enclosed in the hydrogel. In some embodiments of aspects provided herein, the method further comprises: (d) removing the hydrogel from the surface of the substrate.

In some embodiments of aspects provided herein, the method further comprises, in (a), stretching an additional nucleic acid molecule on the surface of the substrate. In some embodiments of aspects provided herein, the additional nucleic acid molecule is in contact with another two members of the plurality of discrete features, thereby suspending a portion of the additional nucleic acid molecule between the another two members of the plurality of discrete features. In some embodiments of aspects provided herein, each of the plurality of discrete features is independently a pit, a pore, a trough, a channel, a well, a pillar, a bump, a protrusion, a ridge, or a bar. In some embodiments of aspects provided herein, each of the two members of the plurality of discrete features is independently a pillar, a bump, a protrusion, a ridge, or a bar. In some embodiments of aspects provided herein, each of the two additional members of the plurality of discrete features is independently a pillar, a bump, a protrusion, a ridge, or a bar. In some embodiments of aspects provided herein, at least portions of the nucleic acid molecule are enclosed in the hydrogel.

In some embodiments of aspects provided herein, each of the another two members of the plurality of discrete features is independently a pillar, a bump, a protrusion, a ridge, or a bar. In some embodiments of aspects provided herein, the nucleic acid molecule is a deoxyribonucleic acid (DNA). In some embodiments of aspects provided herein, the DNA is double-stranded or single-stranded. In some embodiments of aspects provided herein, the nucleic acid molecule is active in an enzymatic reaction. In some embodiments of aspects provided herein, the method further comprises: performing an enzymatic reaction on the nucleic acid molecule. In some embodiments of aspects provided herein, the method further comprises: performing an enzymatic reaction on the additional nucleic acid molecule. In some embodiments of aspects provided herein, the method further comprises: performing a protein binding reaction, a hybridization reaction, a primer-extension reaction catalyzed by a polymerase, a nicks translation reaction, or a nick extension reaction on the nucleic acid molecule. In some embodiments of aspects provided herein, the method further comprises: performing a protein binding reaction, a hybridization reaction, a primer-extension reaction catalyzed by a polymerase, a nicks translation reaction, or a nick extension reaction on the additional nucleic acid molecule. In some embodiments of aspects provided herein, each of the two members of the plurality of discrete features comprises photoresist.

In some embodiments of aspects provided herein, the method further comprises: before (a), applying a layer of a photoresist on top of the substrate. In some embodiments of aspects provided herein, the method further comprises: before (a), shining ultraviolet light through a mask onto the layer of the photoresist. In some embodiments of aspects provided herein, the removing in (b) comprises developing the layer of the photoresist. In some embodiments of aspects provided herein, each of the two members of the plurality of discrete features comprises the photoresist. In some embodiments of aspects provided herein, each of the two additional members of the plurality of discrete features comprises the photoresist. In some embodiments of aspects provided herein, the photoresist is a positive photoresist or a negative photoresist. In some embodiments of aspects provided herein, before (a), the surface comprises a topographical pattern comprising the plurality of features and a plurality of cavities, wherein each of the plurality of features is independently a pillar, a bump, a protrusion, a ridge, or a bar. In some embodiments of aspects provided herein, each of the plurality of cavities is independently a pit, a pore, a trough, a channel, or a well. In some embodiments of aspects provided herein, the method further comprises: before (a), filling up each of the plurality of cavities with a photoresist. In some embodiments of aspects provided herein, the removing in (b) comprises developing the layer of the photoresist, wherein the photoresist is a negative photoresist. In some embodiments of aspects provided herein, the method further comprises: before (a), shining ultraviolet light onto the photoresist on the surface, wherein the photoresist is a positive photoresist. In some embodiments of aspects provided herein, the removing in (b) comprises developing the layer of the positive photoresist.

In another aspect, the present disclosure provides a system comprising: (a) a substrate comprising a surface, the surface comprising a plurality of discrete features; and (b) a nucleic acid molecule in contact with two members of the plurality of discrete features.

In some embodiments of aspects provided herein, a portion of the nucleic acid molecule is suspended between the two members of the plurality of discrete features. In some embodiments of aspects provided herein, the nucleic acid molecule is in contact with two additional members of the plurality of discrete features. In some embodiments of aspects provided herein, an additional portion of the nucleic acid molecule is suspended between the two additional members of the plurality of discrete features. In some embodiments of aspects provided herein, the plurality of discrete features form a topographical pattern.

In some embodiments of aspects provided herein, the system further comprises a hydrogel on the surface, the hydrogel being in contact with some or all members of the plurality of discrete features. In some embodiments of aspects provided herein, at least portions of the nucleic acid molecule are enclosed in the hydrogel. In some embodiments of aspects provided herein, the nucleic acid molecule is stretched. In some embodiments of aspects provided herein, each of the plurality of discrete features is independently a pit, a pore, a trough, a channel, a well, a pillar, a bump, a protrusion, a ridge, or a bar. In some embodiments of aspects provided herein, each of the two members of the plurality of discrete features is independently a pillar, a bump, a protrusion, a ridge, or a bar. In some embodiments of aspects provided herein, each of the two additional members of the plurality of discrete features is independently a pillar, a bump, a protrusion, or a bar.

In some embodiments of aspects provided herein, the nucleic acid molecule is a deoxyribonucleic acid (DNA). In some embodiments of aspects provided herein, the DNA is double-stranded or single-stranded. In some embodiments of aspects provided herein, the nucleic acid molecule is active in an enzymatic reaction. In some embodiments of aspects provided herein, the nucleic acid molecule is active in a protein binding reaction, a hybridization reaction, a primer-extension reaction catalyzed by a polymerase, a nicks translation reaction, or a nick extension reaction. In some embodiments of aspects provided herein, each of the two members of the plurality of discrete features comprises a photoresist. In some embodiments of aspects provided herein, the photoresist is a positive photoresist or a negative photoresist. In some embodiments of aspects provided herein, each of the two additional members of the plurality of discrete features comprises a photoresist. In some embodiments of aspects provided herein, the photoresist is a positive photoresist or a negative photoresist. In some embodiments of aspects provided herein, the system further comprises an additional nucleic acid in contact with another two members of the plurality of discrete features. In some embodiments of aspects provided herein, each of the two members of the plurality of discrete features comprises no photoresist.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
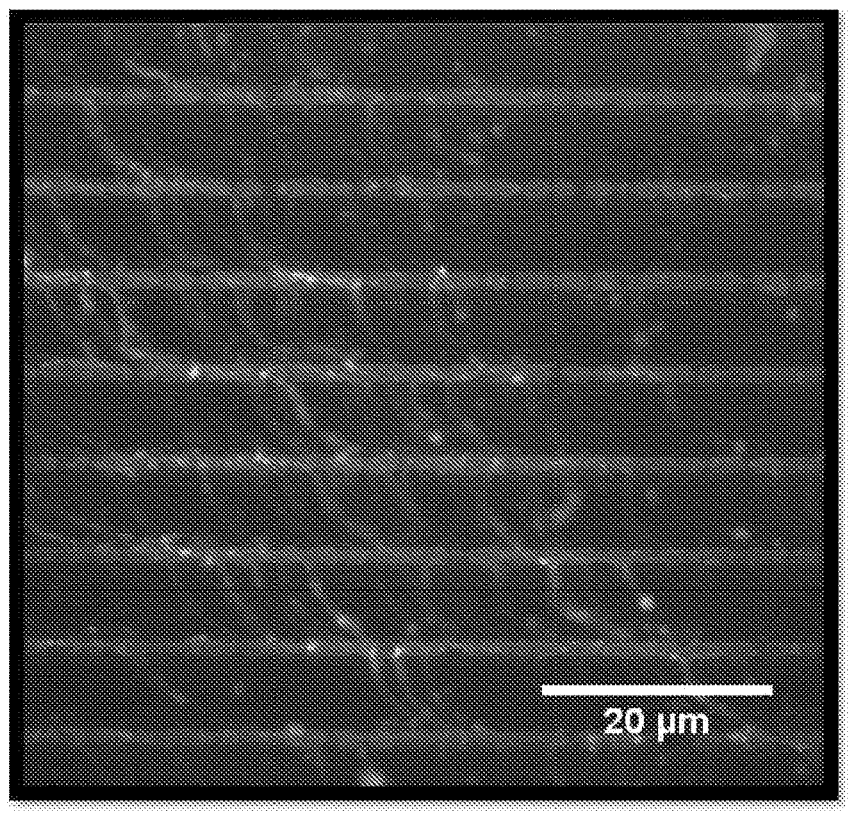
FIG. 1 shows a picture of SU-8 pillars with DNA molecules stretched across the surface features (SU-8 bars).

There is a great interest in capturing and aligning DNA molecules that are enzymatically active. For example, the captured DNA can serve as a template for DNA polymerase. Such capture methods can be the foundation for various research and diagnostic methods, including DNA sequencing. Although various methods for combing and stretching DNA molecules have been published, in general, these methods may render the captured DNA molecules less conducive to further enzymatic reactions. Stretching DNA across a surface may be a useful method to investigate the genome. However, surface effects may limit the ability of enzymes to gain access to and manipulate DNA. For example, a DNA molecule lying on a solid surface may limit the accessible interaction with an approaching enzyme to only one side of the DNA molecule because the other side is blocked by the surface.

The present disclosure provides methods to suspend DNA molecules through intermittent "pillars" or capture bars so that the DNA molecules can be suspended over a plurality of pillars or capture bars. The suspended segments of the DNA molecules, for example, a segment of the DNA molecule not lying on top of a pillar or capture bar, can be submerged in a buffer solution, inside hydrogels or otherwise available for enzymatic reactions. Thus, an enzyme can gain access to this segment from both sides of the DNA molecule when compared with a DNA molecule lying on a solid surface. In one embodiment, DNA molecules can be stretched across a photoresist surface. At some intervals of space, such as, for example, from about 1 µM to about 200 µM, a UV light can be applied, for example, through a mask, to crosslink the DNA to the photoresist. In another embodiment, the UV light can also be used to build the capture bars or "pillars" underneath the crosslinked DNA. The combined results may lead to some segments of the DNA molecules being suspended on top of the capture bars or pillars. In another embodiment, a photoresist (such as SU-8 or poly(methyl methacrylate) (PMMA) based photoresists) can be exposed to light in a specific pattern. Then DNA can be stretched on the exposed photoresist. The photoresist is then developed such that the exposed part and the unexposed part may react different in a treatment, such as a chemical treatment, to result in capture bars or pillars with DNA molecules suspended on top of a plurality of capture bars or pillars. In yet another embodiment, a patterned surface such as PMMA or SU-8 based surface with pillars can be used. The gaps between pillars can be filled with a second material. DNA can be stretched over the surface and then the second material, such as, for example, a hydrogel, can be removed to suspend the DNA fragments. This platform can be used for DNA sequencing, mapping and other applications. In one embodiment, DNA molecules can be suspended and then the suspended DNA can be transferred to a hydrogel and hybridized with primers. Single molecule sequencing can be performed by primer extension using, e.g., reversible terminators from multiple extension sites.

The term "oligonucleotide" as used herein generally refers to a nucleotide chain. In some cases, an oligonucleotide is less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligonucleotide (e.g., a primer). Oligonucleotides can comprise natural nucleotides, non-natural nucleotides, or combinations thereof.

The term "about" as used herein generally refers to +/−10%, 9%, 8%, 7%, 6%, 5%, 4%, 3%, 2%, or 1% of the designated amount.

As used herein, the term "substantially," when describing a relative value, a relative amount or a relative degree between two subjects, generally refers to within 80%, 81%, 82%, 83%, 84%, 85%, 86%, 87%, 88%, 89% 90%, 91%, 92%, 93%, 94%, 95%, 96%, 97%, 98%, 99%, 100%, 101%, 102%, 103%, 104%, 105%, 106%, 107%, 108%, 109%, or 110% of each other in value, amount or degree.

As used herein, open terms, for example, "comprise", "contain", "include", "including", "have", "having" and the like refer to comprising unless otherwise indicates.

The term "immobilization" as used herein generally refers to forming a covalent bond between two reactive groups. For example, polymerization of reactive groups is a form of immobilization. A covalent bond formation between two atoms, such as, for example, Carbon atom and Carbon atom, Carbon atom and hetero atom, and hetero atom and hetero atom, is an example of immobilization when the two atoms are from the two reactive groups, respectively.

As used herein, the term "substrate" or "solid substrate" generally refers to a substance, structure, surface, material, means, or composition, which comprises a nonbiological, synthetic, nonliving, planar, spherical or flat surface. The substrate may include, for example and without limitation, semiconductors, synthetic metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics; nanostructures and microstructures. The substrate may comprises an immobilization matrix such as but not limited to, insolubilized substance, solid phase, surface, layer, coating, woven or nonwoven fiber, matrix, crystal, membrane, insoluble polymer, plastic, glass, biological or biocompatible or bioerodible or biodegradable polymer or matrix, microparticle or nanoparticle. Other example may include, for example and without limitation, monolayers, bilayers, commercial membranes, resins, matrices, fibers, separation media, chromatography supports, polymers, plastics, glass, mica, gold, beads, microspheres, nanospheres, silicon, gallium arsenide, organic and inorganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes. The substrate can exist as one or more particles, strands, precipitates, gels, sheets, tubing, spheres, containers, capillaries, pads, slices, films, plates, slides, or semiconductor integrated chips, for example. The substrate can be flat or can take on alternative surface configurations. For example, the substrate can contain raised or depressed regions on which synthesis or deposition takes place. In some examples, the substrate can contain raised or depressed regions in different 3-D shapes and/or heights. In some examples, the substrate can comprise a plurality of features. In some examples, the substrate can comprise a topographical pattern and the topographical can comprise a group of troughs, a group of bars, a group of pillars, a group of well, or a combination thereof. In some cases, the topographical pattern can be formed by at least two different materials, for example, a silicon chip covered with a layer of photoresist, or a quartz chip covered with a hydrogel, etc. In some examples, the substrate can contain raised or depressed regions in substantially the same 3-D shapes and/or heights. In some examples, the substrate can be chosen to provide appropriate light-absorbing characteristics. For example, the substrate can be a polymerized Langmuir Blodgett film, functionalized glass (e.g., controlled pore glass), silica, titanium oxide, aluminum oxide, indium tin oxide (ITO), Si, Ge, GaAs, GaP, $SiO_2$, $SiN_4$, modified silicon, the top dielectric layer of a semiconductor integrated circuit (IC) chip, or any one of a variety of gels or polymers such as (poly)tetrafluoroethylene, (poly)vinylidenedifluoride, polystyrene, polycarbonate, polydimethylsiloxane (PDMS), poly(methyl methacrylate) (PMMA), polycyclicolefins, or combinations thereof.

The substrates can comprise polymer coatings or gels, such as a polyacrylamide gel or a PDMS gel. Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, betaine acrylamide monomers, and combinations thereof.

As used herein, the term "nucleic acid" generally refers to a polymer comprising one or more nucleic acid subunits or nucleotides. A nucleic acid may include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double-stranded.

As used herein, the term "adjacent" or "adjacent to," includes "next to," "adjoining," and "abutting." In one example, a first location is adjacent to a second location when the first location is in direct contact and shares a common border with the second location and there is no space between the two locations. In some cases, the adjacent is not diagonally adjacent.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by ILLUMINA®, Pacific Biosciences (PACBIO®), Oxford NANOPORE®, or Life Technologies (ION TORRENT®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "nucleic acid sequence" or "nucleotide sequence" as used herein generally refers to nucleic acid molecules with a given sequence of nucleotides, of which it may be desired to know the presence or amount. The nucleotide sequence can comprise ribonucleic acid (RNA) or DNA, or a sequence derived from RNA or DNA. Examples of nucleotide sequences are sequences corresponding to natural or synthetic RNA or DNA including genomic DNA and messenger RNA. The length of the sequence can be any length that can be amplified into nucleic acid amplification products, or amplicons, for example, up to about 20, 50, 100, 200, 300, 400, 500, 600, 700, 800, 1,000, 1,200, 1,500, 2,000, 5,000, 10,000 or more than 10,000 nucleotides in length, or at least about 20, 50, 100, 200, 300, 400, 500, 600, 700, 800, 1,000, 1,200, 1,500, 2,000, 5,000, 10,000 or 10,000 nucleotides in length.

The term "template" as used herein generally refers to individual polynucleotide molecules from which another nucleic acid, including a complementary nucleic acid strand, can be synthesized by a nucleic acid polymerase. In addition, the template can be one or both strands of the polynucleotides that are capable of acting as templates for template-dependent nucleic acid polymerization catalyzed by the nucleic acid polymerase. Use of this term should not be taken as limiting the scope of the present disclosure to polynucleotides which are actually used as templates in a subsequent enzyme-catalyzed polymerization reaction. The template can be an RNA or DNA. The template can be cDNA corresponding to an RNA sequence. The template can be DNA.

As used herein, "amplification" of a template nucleic acid generally refers to a process of creating (e.g., in vitro) nucleic acid strands that are identical or complementary to at least a portion of a template nucleic acid sequence, or a universal or tag sequence that serves as a surrogate for the template nucleic acid sequence, all of which are only made if the template nucleic acid is present in a sample. Typically, nucleic acid amplification uses one or more nucleic acid polymerase and/or transcriptase enzymes to produce multiple copies of a template nucleic acid or fragments thereof, or of a sequence complementary to the template nucleic acid or fragments thereof. In vitro nucleic acid amplification techniques are may include transcription-associated amplification methods, such as Transcription-Mediated Amplification (TMA) or Nucleic Acid Sequence-Based Amplification (NASBA), and other methods such as Polymerase Chain Reaction (PCR), Reverse Transcriptase-PCR (RT-PCR), Replicase Mediated Amplification, and Ligase Chain Reaction (LCR).

As used herein, the term "hydrogel" generally refers to a gel in which the swelling agent is water. The term "gel" refers to a non-fluid colloidal network or polymer network that is expanded through its volume by a fluid. The term "swelling agent" is a fluid used to swell a gel or network. For example, water can be a swelling agent for a hydrogel. The hydrogels of the present disclosure may be prepared by polymerization of one or more acrylamide-functionalized monomers. For example, an acrylamide tail can also be bonded to the surface of a substrate, for example, a quartz slide. Then a solution containing acrylamide monomers can be brought in contact with the surface bonded with acrylamide tails. Then the poured solution can be subject to polymerization of acrylamide monomers and the acrylamide tails such that a hydrogel can be formed. In some cases, the hydrogel of the present disclosure comprises polyacrylamides. In some cases, the hydrogel of the present disclosure comprises crossed lined polyacrylamides. In some cases, the hydrogel of the present disclosure comprises about 0.5%, 1%, 2%, 3%, 4%, 5%, 6%, 7%, 8%, 9%, 10%, 11%, 12%, 13%, 14%, 15%, 16%, 17%, 18%, 19%, or 20% of polyacrylamides in weight. In some cases, the hydrogel can be obtainable by combining acrylamide and methylene bis-acrylamide. The polymerization reaction can be radical initiated by an initiator. The hydrogel can be obtained by combining acrylamide and methylene bis-acrylamide is in a molar ratio of 150:1 to 1000:1 in the presence of a radical initiator. Methylene bis-acrylamide can provide cross-linking between polymer chains and the molar ratio may be varied to provide various cross-linking densities of the hydrogel. The conditions for obtaining the hydrogel may be modified. Ammonium persulfate (AMPS) can be used as an initiator for the polymerization.

Combed DNA on Surface

In some cases, DNA molecules can be combed or stretched on a surface. However, previously reported combed or stretched DNA molecule on a surface may be limited in its ability to serve as a template for polymerase reaction. In one aspect of the invention, a method is provided for placing a stretched DNA molecule on a surface and the stretched DNA molecule is placed on patterned bars or pillars. As shown in FIG. 1, DNA molecules can be stretched on top of a plurality of patterned bars made from photo resist, such as, for example, SU-8. Various embodiments can be employed to suspend DNA with intermittent pillars or capture bars or patterns of materials made from a photoresist. The DNA molecule on the surface of the substrate may comprise two types of DNA segments: the first type (hereinafter referred to as "the anchoring segment") is in touch with the top of a pillar or capture bar; and the second type (hereinafter referred to as "the suspended segment") is in-between two adjacent anchoring segments such that the DNA of the suspended segment is suspended in-between the two pillars or capture bars nearby. The anchoring segments and the suspended segments can be in tandem. The suspended segments of the DNA molecule can be more accessible to enzymes and primers for enzymatic reactions than a DNA molecule on a surface without pillars or capture bars. The suspended segments of the DNA can be submerged in a buffer or a hydrogel, thereby subjected to an enzymatic reaction.

The present disclosure provides several methods to construct suspended DNA on a surface with pillars or capture bars, or other features. DNA stretching on a surface can be obtained by several methods: Meniscus retraction, flow fields, mechanical treading and others. Surfaces can be patterned with a wide range of techniques and a large variety of materials can be used.

A DNA molecule, such as, for example, a genomic DNA molecule, may be stretched by all kinds of means, including but not limited to, using alternating current (AC) electric fields (Kaji, N., "Molecular stretching of long DNA in agarose gel using alternating current electric fields," *Biophys. J.*, 82(1 Pt 1):335-44, 2002), using an electric field gradients in a phyperbolic contraction microchannel (Randall, G. C., et al., "Methods to electrophoretically stretch DNA: microconstractions, gels, and hybrid gel-microconstraction devices," *Lab. Chip*, 6(4):516-25, 2006), with optical tweezers uniform flows (Smith, S. B., et al., "Overstretching B-DNA: the elastic response of individual double-stranded and single-stranded DNA molecules," *Science*, 271: 795-9, 1996), with uniform flows (Perkins, T. T., et al., "Stretching of a single tethered polymer in a uniform flow," *Science*, 268: 83-7, 1995), with uniform electric fields (Ferree, S., et al., "Electrokinetic stretching of tethered DNA," *Biophys. J.*, 85(4):2539-46, 2003), using acoustic force spectroscopy (AFS) (Sitters, G., et al., "Acoustic force spectroscopy," *Nat. Methods*, 12(1):47-50, 2015), forcing DNA into a nanochannel (Tegenfeldt, J. O., et al., "The dynamics of genomic-length DNA molecules in 100-nm channels," *Proc. Nat. Acad. Sci. U.S.A.*, 101(30):10979-83, 2004), hydrodynamic focusing of multiple streams (Wong, P. K., et al., "Deformation of DNA molecules by hydrodynamic focusing," *J Fluid. Mech.*, 497:55-65, 2003), and dynamic combing onto a surface (Dimalanta, E. T., et al., "A microfluidic system for large DNA molecule arrays," *Anal. Chem.*, 76(18):5293-301, 2004).

Figure 2A:
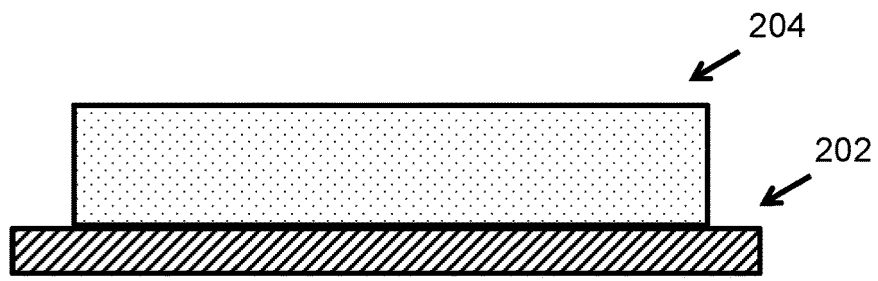
FIGS. 2A-2D depict a schematic process of generating a DNA molecule suspended on top of surface features using DNA cross-linking methods.
Figure 2B:
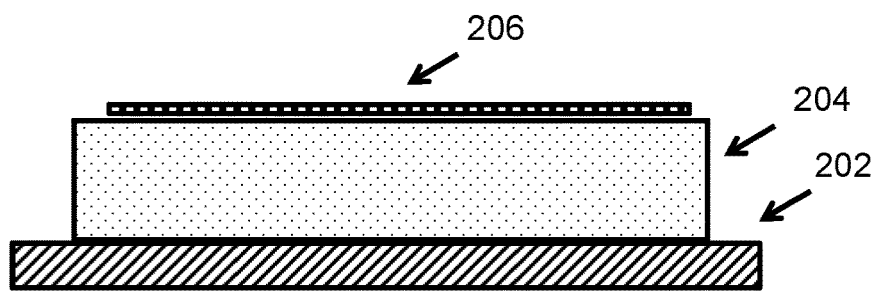
Figure 2C:
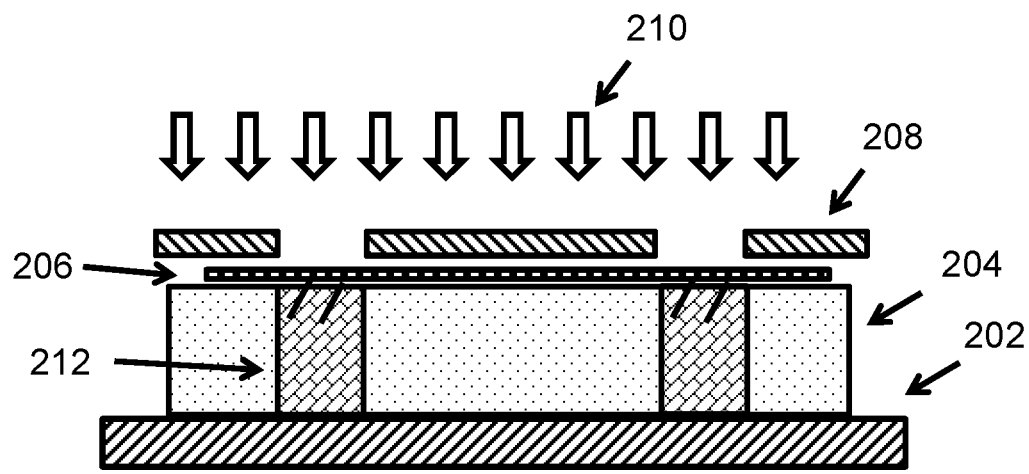
Figure 2D:
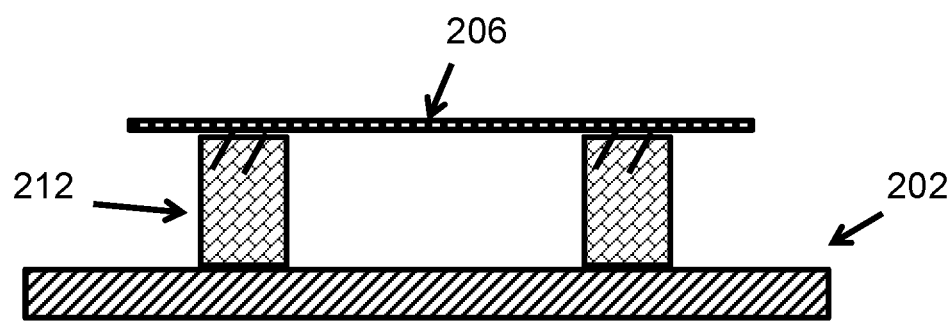

FIG. 1 shows genomic DNA can be stretched across SU-8 photoresist patterned bars. In this case, the SU-8 bars are shown as horizontal bars separated by troughs. As shown in FIG. 1, the width of the bar is much smaller than the width of the trough. The stretched DNA can be seen suspended between adjacent bars, similar to threads of fabrics lying across the mesh shelf of a drying rack. Because combed or stretched DNA can be suspended on intermittent pillars or capture bars or other patterns on a surface of a substrate, the suspended parts of the DNA (e.g., the parts that are over the troughs in FIG. 1) can be more accessible to enzymes and/or primers or other biomolecules for reactions to happen. For example, the suspended part can be submerged in buffer or in hydrogel FIGS. 2A-2D show an example scheme of the disclosed method of suspending DNA. In this example, the nucleic acid is captured by ultraviolet (UV) crosslinking to pillar or bars. The capture points, e.g., approximately about every 10 µM to about every 100 µM, can be created by photo mask patterns. FIG. 2A shows a layer 204 of photoresist on top of the substrate 202. FIG. 2B shows a stretched nucleic acid 206 on top of the layer 204 of the photoresist. FIG. 2C shows a mask 208 with patterns can be placed above the stretched nucleic acid 206 and the layer 204 of the photoresist. Then the layer 204 of the photoresist can be exposed to the ultraviolet light 210 through the mask 208. The exposed portions of the nucleic acid 206 may form covalent bonds with the exposed portions 212 of the photoresist. FIG. 2D shows after developing the exposed photoresist (e.g., a negative photoresist), portions of the photoresist can be removed, leaving the stretched nucleic acid 206 suspended between the remaining photoresist features (e.g., pillars or bars 212) on the surface of the substrate 202.

Figure 3A:
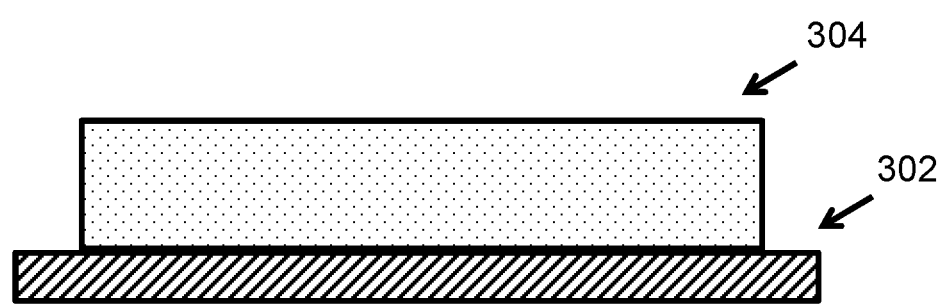
FIGS. 3A-3D show a schematic process of generating a DNA molecule suspended on top of surface features placing DNA on an exposed surface of a photoresist.
Figure 3B:
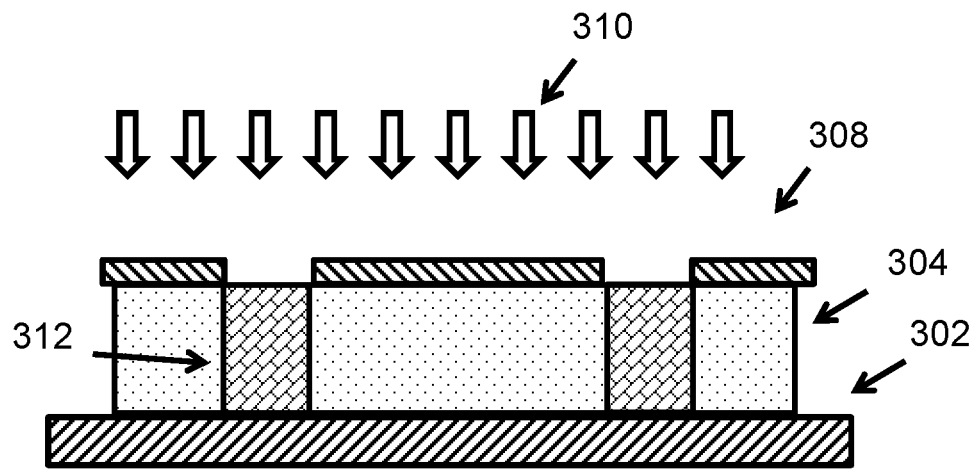
Figure 3C:
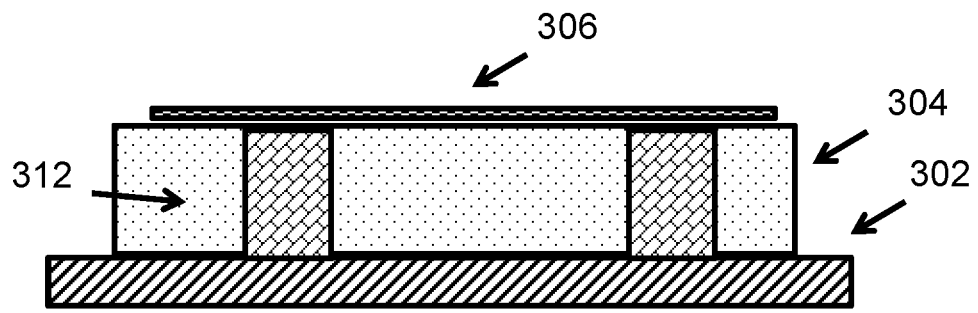
Figure 3D:
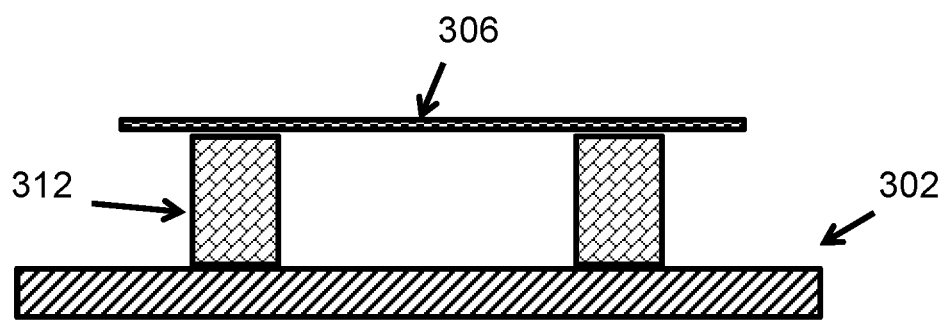

Alternatively, FIGS. 3A-3D show another example scheme of the disclosed method of suspending DNA. In this example, the photoresist layer is exposed before nucleic acid is stretched on top of the photoresist layer. FIG. 3A shows a layer 304 of photoresist on top of the substrate 302. FIG. 3B shows a mask 308 with patterns can be placed above the layer 304 of the photoresist. Then the layer 304 of the photoresist can be exposed to the ultraviolet light 310 through the mask 308. The exposed portions 312 of the photoresist can be formed within the layer 304 of the photoresist. FIG. 3C shows a stretched nucleic acid 306 on top of the layer 304 of the photoresist comprising the exposed portions 312. FIG. 3D shows after developing the exposed photoresist (e.g., a negative photoresist), portions of the photoresist can be removed, leaving the stretched nucleic acid 306 suspended between the remaining photoresist features (e.g., pillars or bars 312) on the surface of the substrate 302.

As shown herein, a nucleic acid can be stretched on a photoresist such as SU-8 that has been exposed to UV light. After the nucleic acid is stretched on top of the photoresist, the photoresist can then be developed without resulting in too much loss of the nucleic acid. The dimensions of the pillar or capture bar or surface features to suspend the stretched nucleic acid may be affected the need to capture DNA and the methods of manufacturing or producing features on the surface of the substrate. For example, the dimensions of the pillar or capture bar or surface features can be in from nanometer range to micrometer range, and in some cases, to minimize the dimension of the capture regions (e.g., top of the pillars, bars, or surface features) in contact with the suspended nucleic acid. In some cases, DNA on the capture regions is less reactive toward enzymatic reactions (e.g., polymerase-catalyzed chain elongation, nick extension, endonuclease reaction, etc.) or other biological reactions (e.g., hybridization).

Figure 4A:
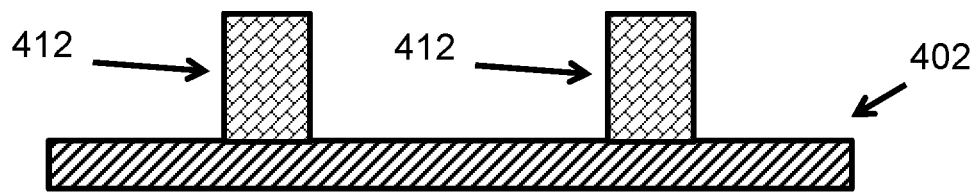
FIGS. 4A-4D depict a schematic process of generating a DNA molecule suspended on top of surface features by filling a second material in gaps of a patterned surface.
Figure 4B:
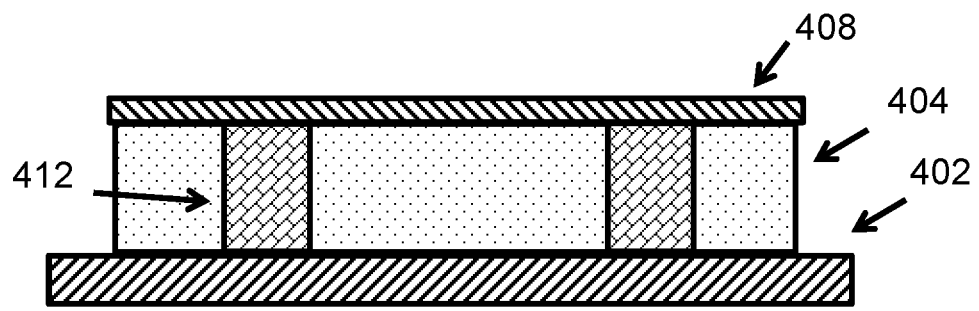
Figure 4C:
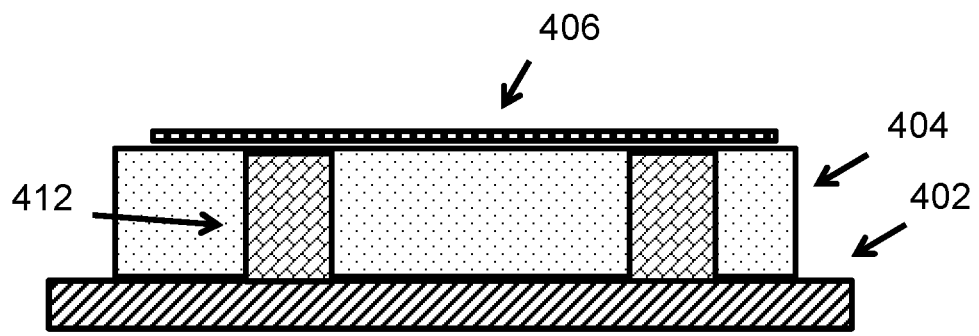
Figure 4D:
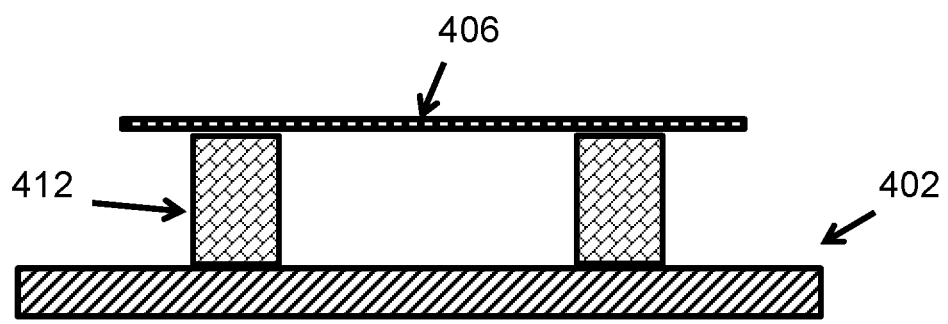

FIGS. 4A-4D show still another example scheme of the disclosed method of suspending DNA. In this example, surface of the substrate 402 can comprise surface features 412 as shown in FIG. 4A. FIG. 4B shows that a filling material 404 can be used to fill up the cavities between the surface features 412 on top the substrate 402 and be covered by a coverslip 408. The filling material 404 may be treated to form a semi-solid or solid form according to the nature of the filling material 404 such that the treated filling material 404 and the surface features 412 together may form a substantially flat surface for the stretched nucleic acid 406 to lay down. Then the filling material 404 can be removed by another treatment. For example, the filling material 404 can be a negative photoresist. FIG. 4D shows the resulting stretched nucleic acid 406 suspended between surface features 412 on the substrate 402.

The stretched nucleic acid suspended between surface features can be further processed with a hydrogel to enclose the stretched nucleic acid. For example, a hydrogel (such as a 6% polyacrylamide gel) can be used to cover the surface cavities shown in FIGS. 2D, 3D, and 4D between the surface features (or pillars or bars) 212, 312 or 412. The hydrogel together with the nucleic acid can then be separated from the substrate (and the surface features). Nucleic acid molecules can then be captured within the gel or on top of the gel.

Figure 5:
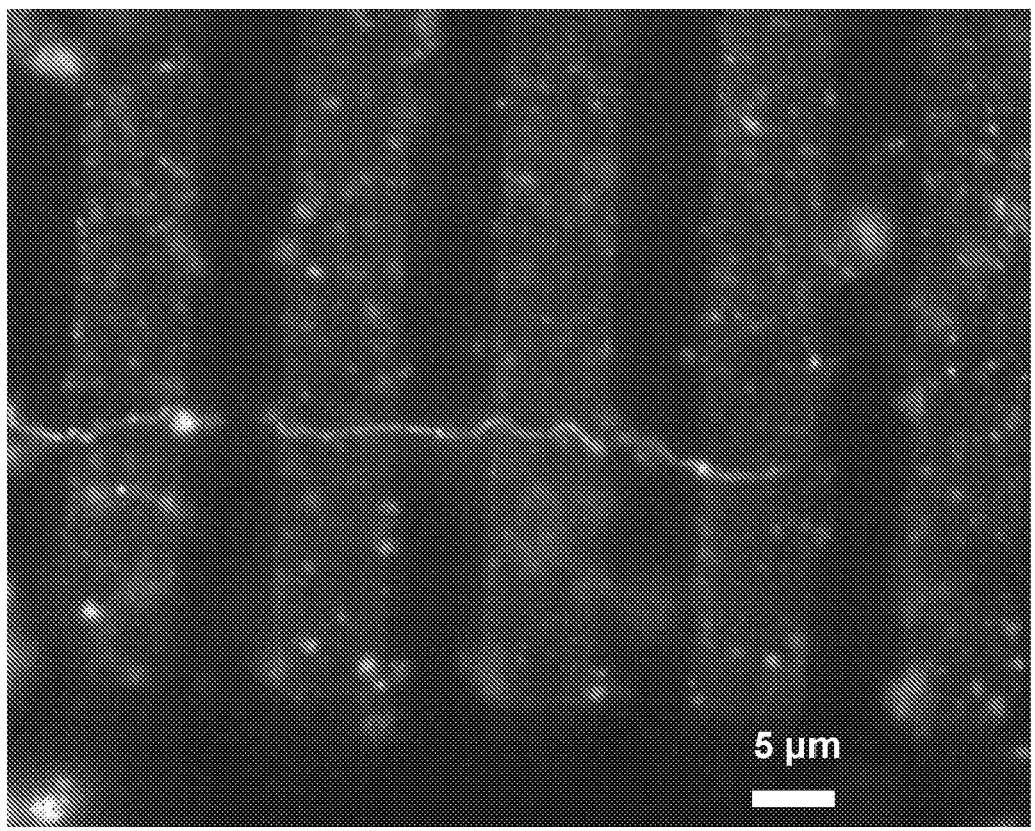
FIG. 5 shows another picture of SU-8 bars with DNA molecules stretched cross the pillars.
Figure 6:
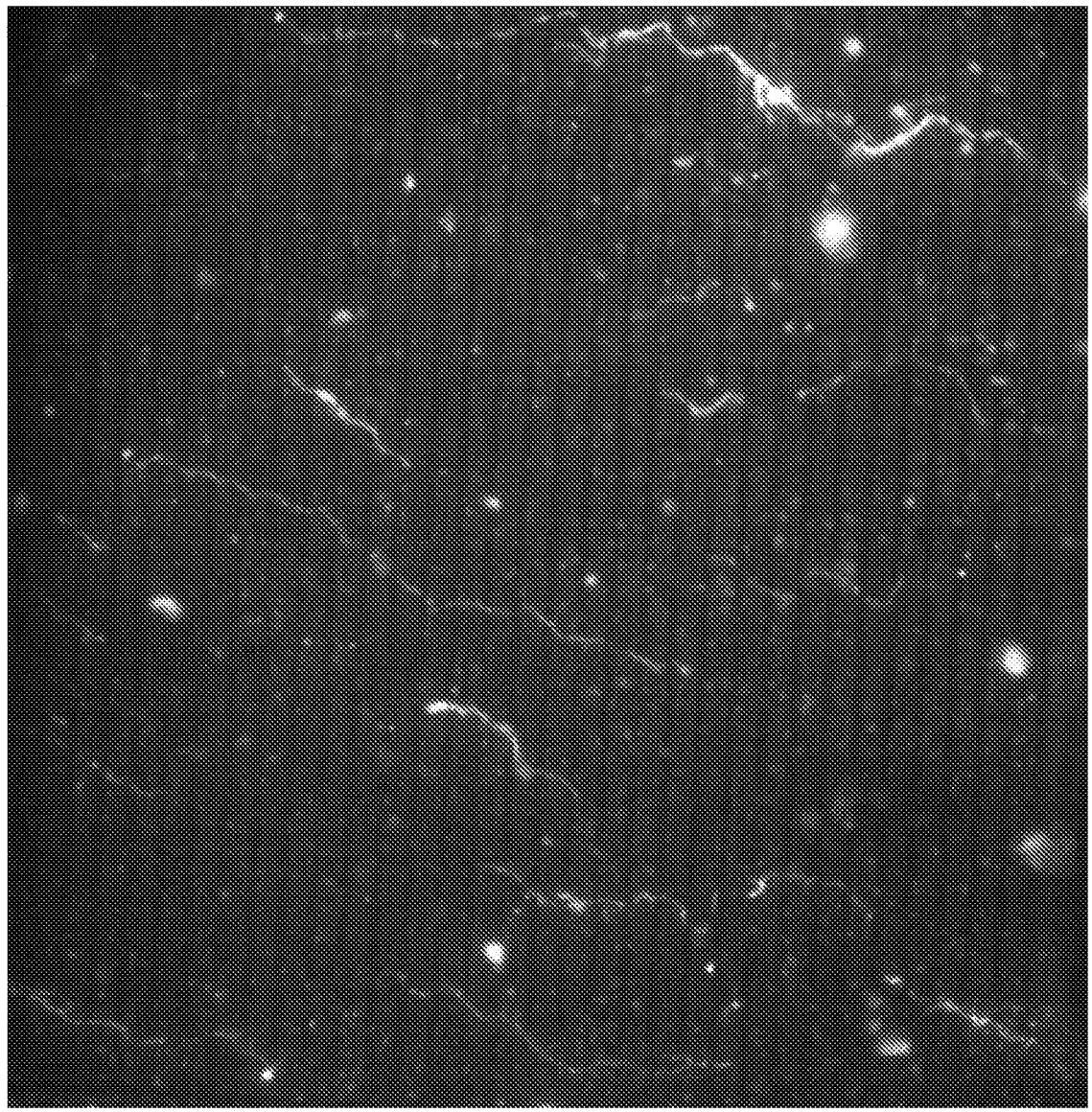
FIG. 6 depicts another picture of SU-8 bars with DNA molecules stretched across the pillars.
Figure 7:
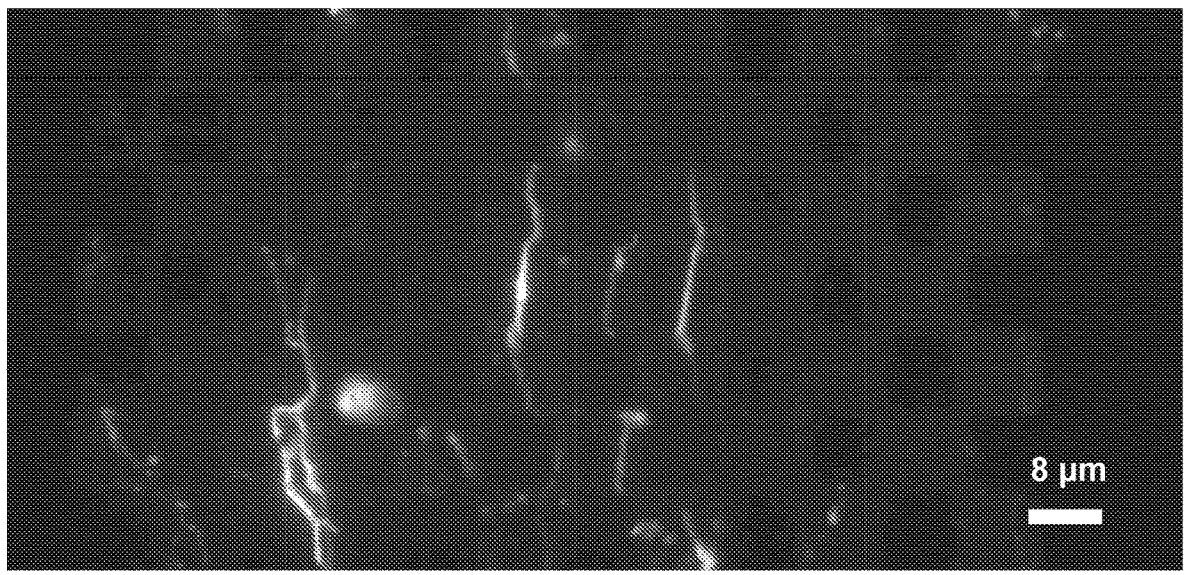
FIG. 7 shows a picture of pillars/capture bars in checkerboard configuration with suspended DNA molecules.
Figure 8:
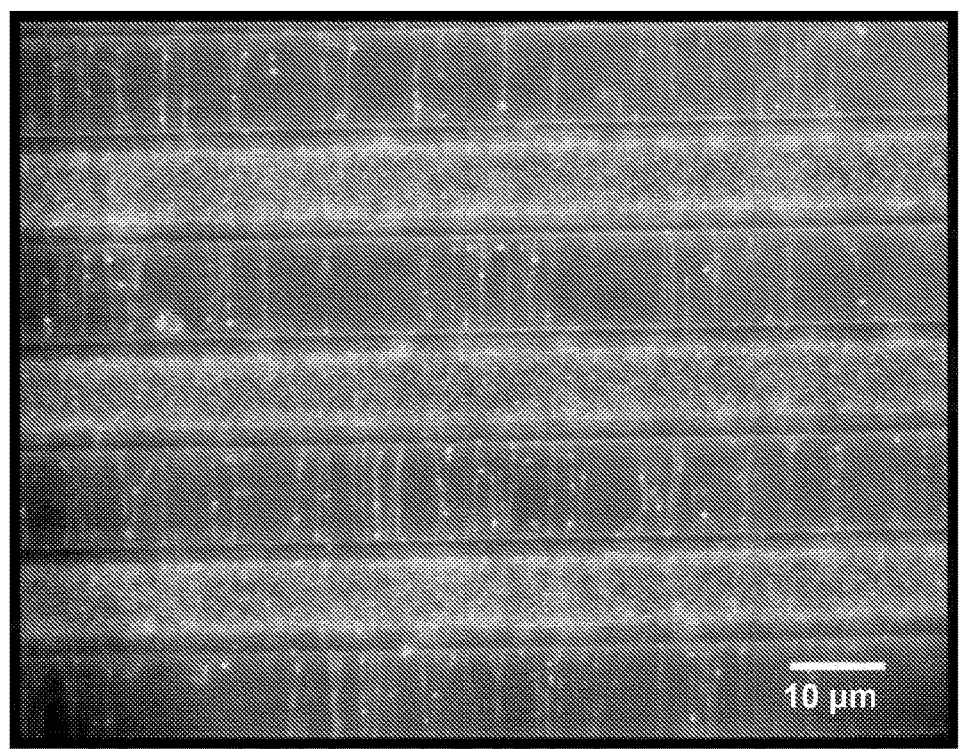
FIG. 8 depicts a picture of both the extension products and the template DNA molecule. The template DNA molecules are suspended across SU-8 lines before the extension reactions.

FIG. 5 shows another example of a nucleic acid molecule (e.g., a DNA molecule) suspended between surface features (e.g., SU-8 bars). The suspended DNA molecules can be relaxed and ready to react with enzymes. FIG. 6 shows that the suspended DNA molecules need not to be very straight when suspended between surface features (e.g., SU-8 bars) because the shape of the DNA molecules can be traced under a microscope or other visual/chemical/biological methods. The shapes of the surface feature can be chosen to facilitate further reactions. FIG. 7 shows a checkerboard pattern for the surface features. One of skill in the art would appreciate that many different patterns can be used as long as there are at least two capture regions in the surface features that can suspend at least one portion of the combed or stretched nucleic acid. FIG. 8 shows nucleic acids (e.g., DNA molecules, shown as thin threads in FIG. 8) can be vertically stretched and suspended across SU-8 horizontal bars (shown as wide bars from left to right in FIG. 8). In addition, the stretched and suspended nucleic acid can be used as a template to extend a primer by incorporating labeled and/or unlabeled nucleotides into the extension products. The labeled nucleotides can appear in colors (e.g., green dots or dots in FIG. 8) along the suspended DNA (shown as nearby red lines, or lines in FIG. 8).

Figure 9:
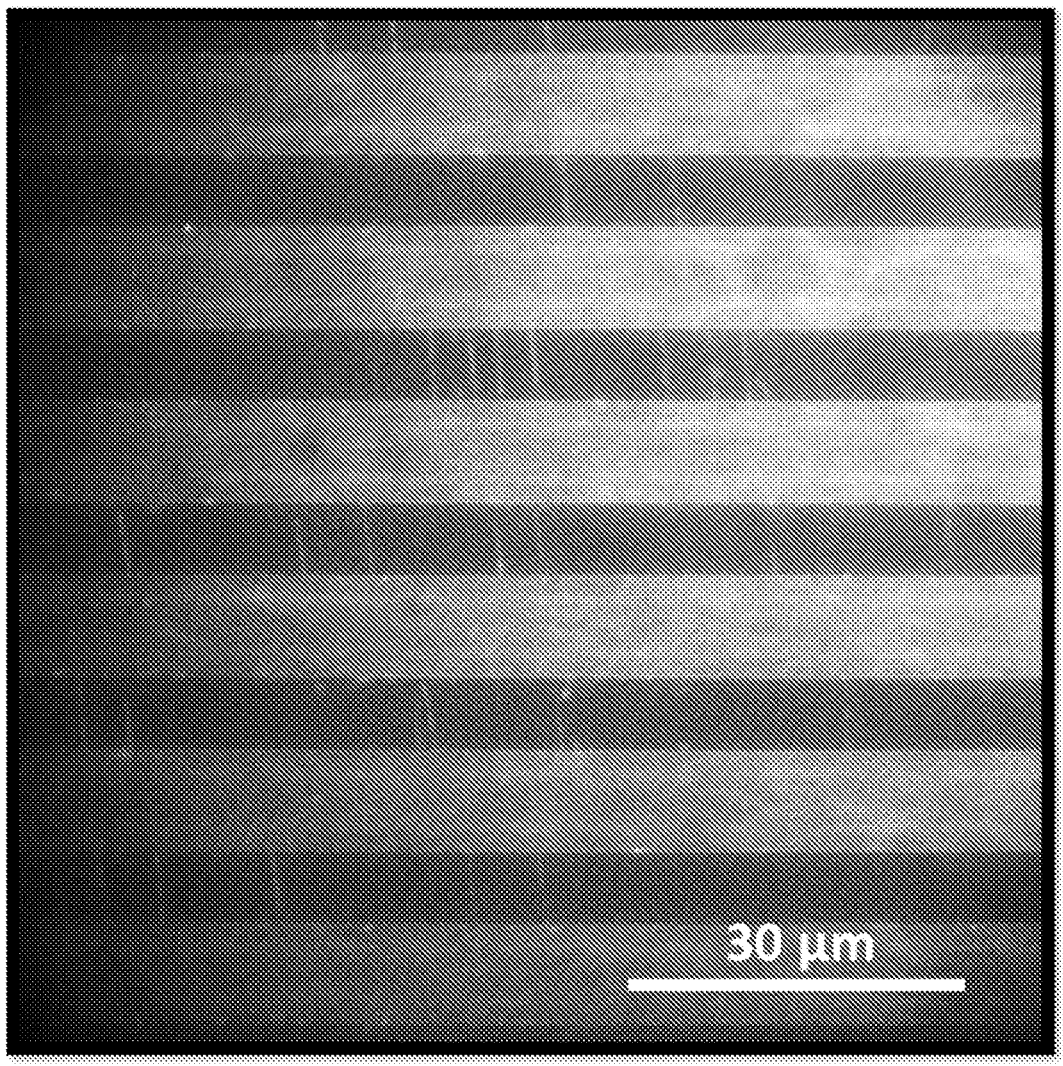
FIG. 9 shows genomic DNA suspended across SU-8 patterned bars.

As shown in FIG. 9, DNA is suspended on top of SU-8 photoresist patterned bars. Various embodiments can be employed to suspend DNA with intermittent capture bars (or other structures) of materials such as a photoresist. The suspended part of the DNA can be more accessible to enzymes and primers for reactions. The suspended parts of the DNA can be submerged in buffer or in a hydrogel.

Figure 10:
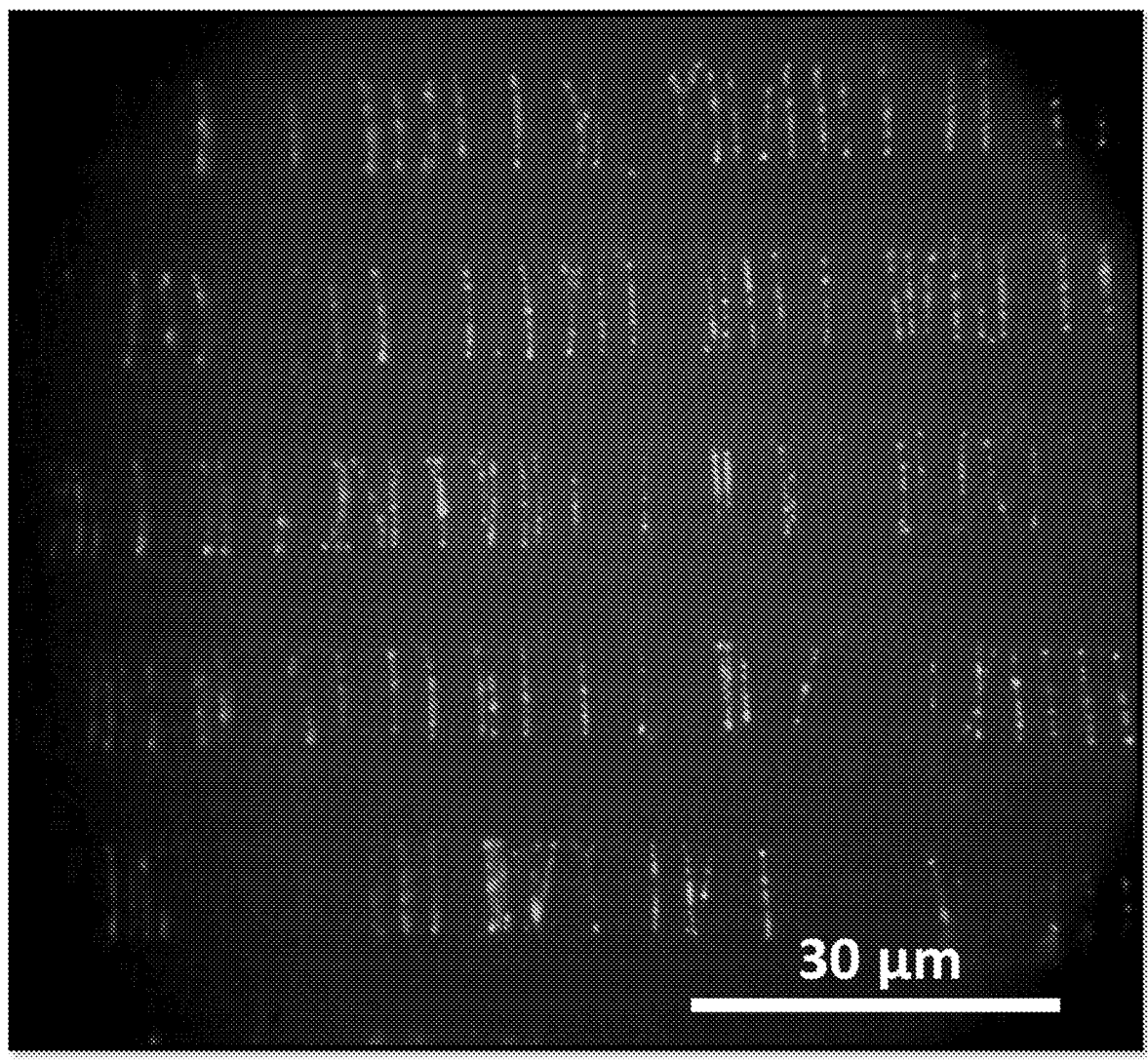
FIG. 10 depicts genomic DNA fragments transferred to a hydrogel.

FIG. 10 shows DNA fragments that have been transferred into a hydrogel. The hydrogel can be formed by pouring reagents onto the suspended DNA over the surface features before the polymerization of the reagents, and the reagents can be covered with a treated surface of a coverslip. Upon the completion of the polymerization, the gel can be separated from the surface features of the substrate, and the DNA fragments can remain trapped in the gel in a substantially linear fashion, similar to that before the gel formation. DNA, stained with an intercalating dye, is rendered in green (or thin lines) in FIG. 10.

Figure 11A:
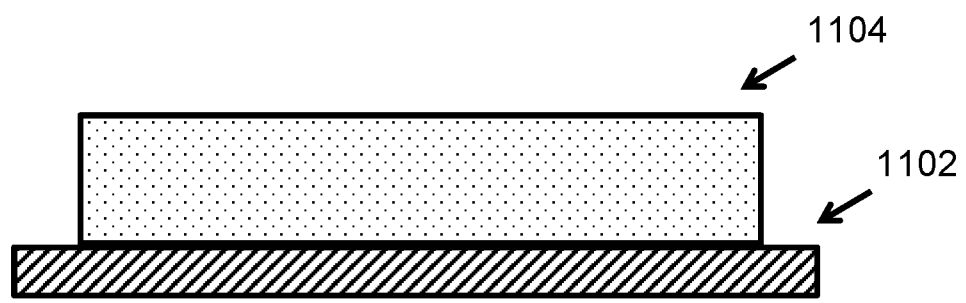
FIGS. 11A-11F show a schematic process of generating stretched DNA molecules in a hydrogel.
Figure 11B:
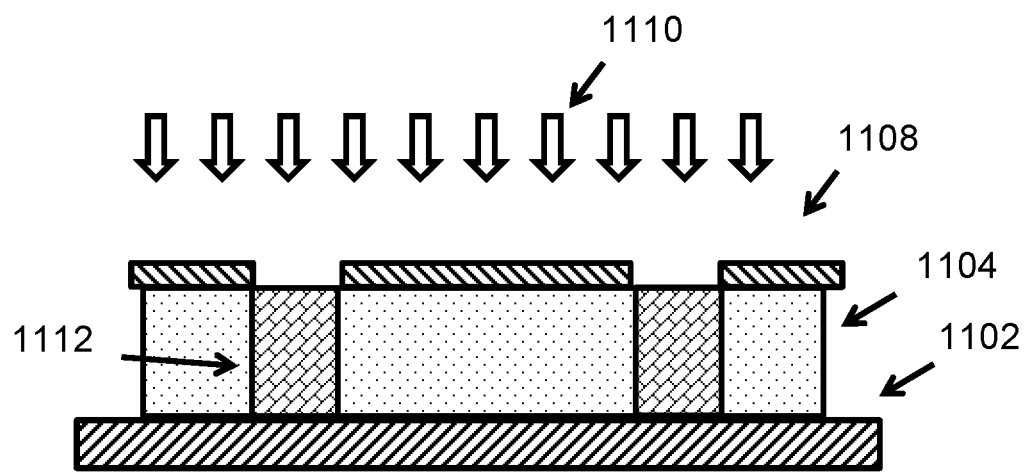
Figure 11C:
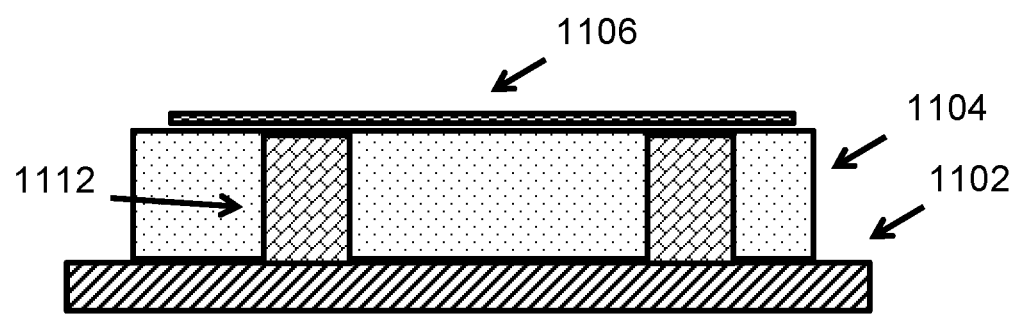
Figure 11D:
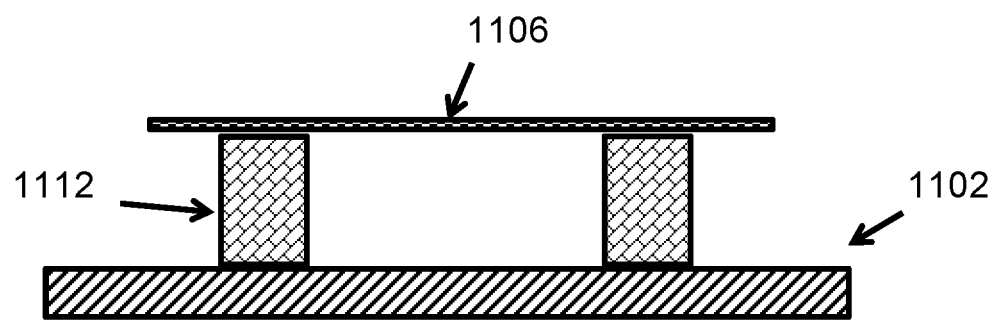
Figure 11E:
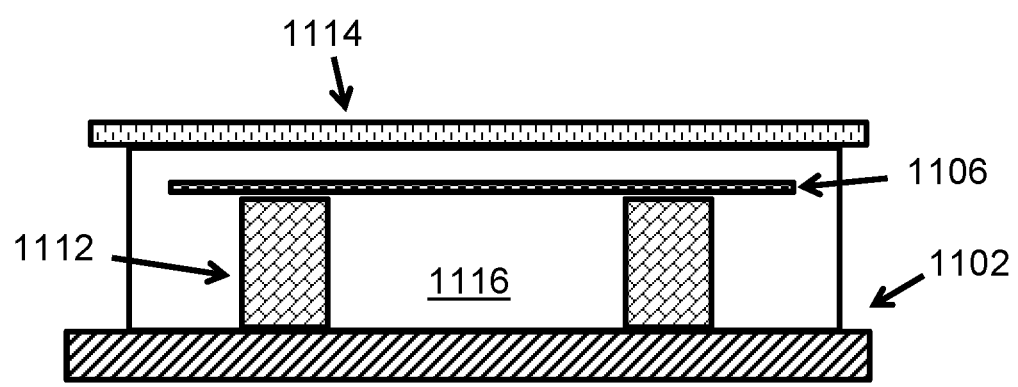
Figure 11F:
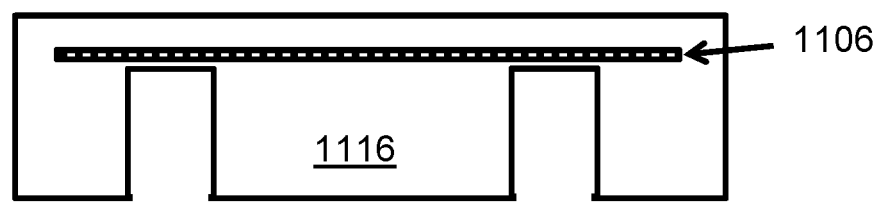

FIGS. 11A-11F show a schematic process to obtain suspended DNA over surface features in FIGS. 9 and 10. In some cases, DNA can be stretched on a photoresist, such as SU-8, that has been exposed to UV light. FIG. 11A shows a layer 1104 of photoresist on top of the substrate 1102. FIG. 11B shows a mask 1108 with patterns can be placed above the layer 1104 of the photoresist. Then the layer 1104 of the photoresist can be exposed to the ultraviolet light 1110 through the mask 1108. The exposed portions 1112 of the photoresist can be formed within the layer 1104 of the photoresist. FIG. 11C shows a stretched nucleic acid 1106 on top of the layer 1104 of the photoresist comprising the exposed portions 1112. FIG. 11D shows that after developing the exposed photoresist (e.g., a negative photoresist), portions of the photoresist can be removed, leaving the stretched nucleic acid 1106 suspended between the remaining photoresist features (e.g., pillars or bars 1112) on the surface of the substrate 1102. FIG. 11E shows reagents for hydrogel 1116 can be pours over the surface of the substrate 1102, filling up the surface cavities between the surface features (or pillars or bars) 1112, and enclosing the suspended, stretched DNA, then covering the reagent with a coverslip 1114. Then polymerization reaction can form the hydrogel 1116 trapping the suspended, stretched DNA 1106 inside the hydrogel. FIG. 11F shows that after the substrate (together with the surface features 1112) is separated from the hydrogel, the suspended, stretched DNA 1106 is trapped within the hydrogel 1116.

Figure 12:
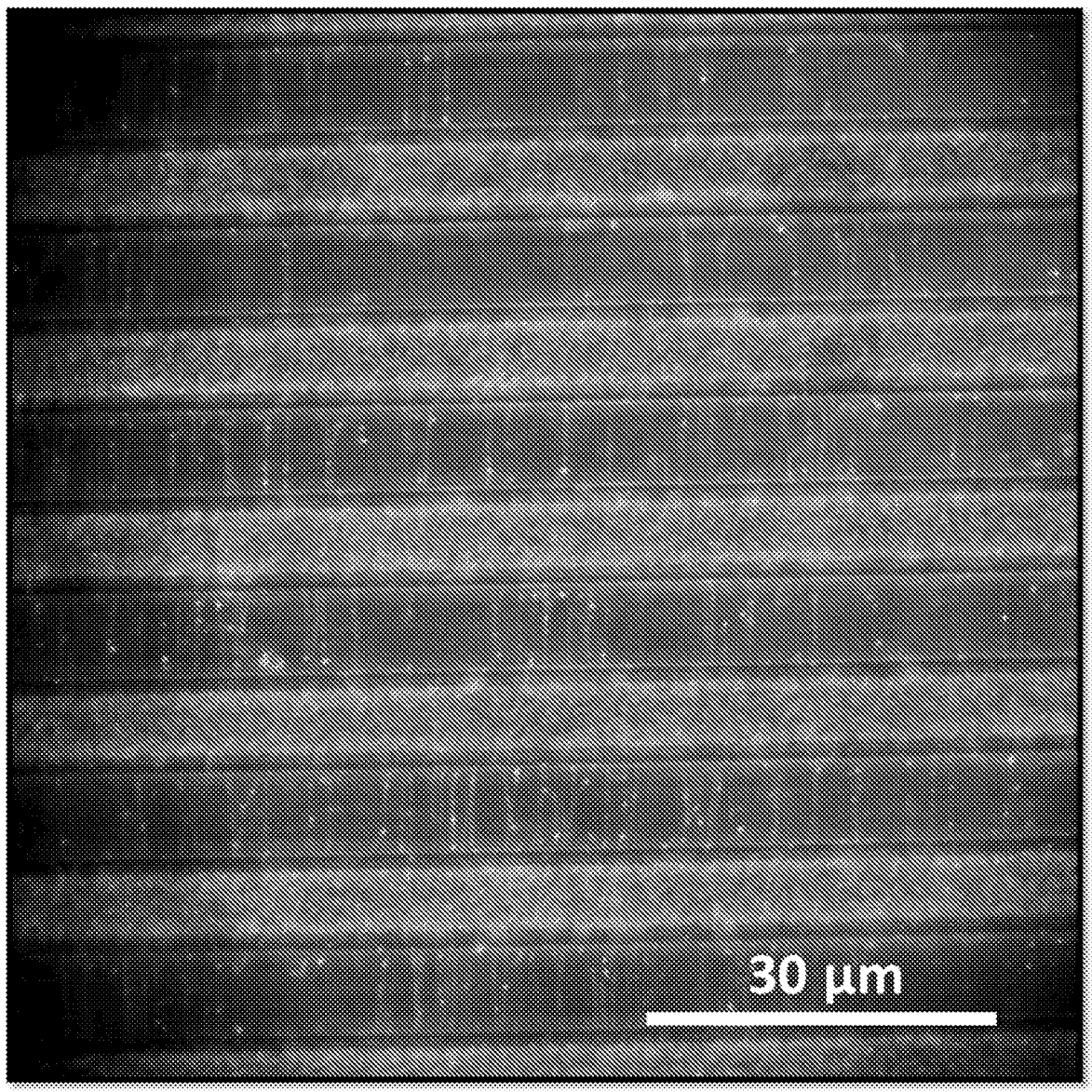
FIG. 12 depicts that DNA vertically suspended across SU-8 horizontal lines, is extended in an aqueous buffer by incorporating labeled and unlabeled nucleotides. The labeled nucleotides appear as green dots (or dots) along the stained DNA (red lines or lines).

FIG. 12 shows genomic DNA molecules suspended across SU-8 bars into an aqueous buffer. DNA can be stained with an intercalating dye and, in this case, the DNA can be rendered in red color (or shown as thin lines) in FIG. 12. Random primers can be extended in the presence of a DNA polymerase using a mixture of labeled and unlabeled nucleotides. The labeled nucleotides can be rendered in green color and appear as dots along the red lines (or lines) of suspended, stretched DNA.

Figure 13:
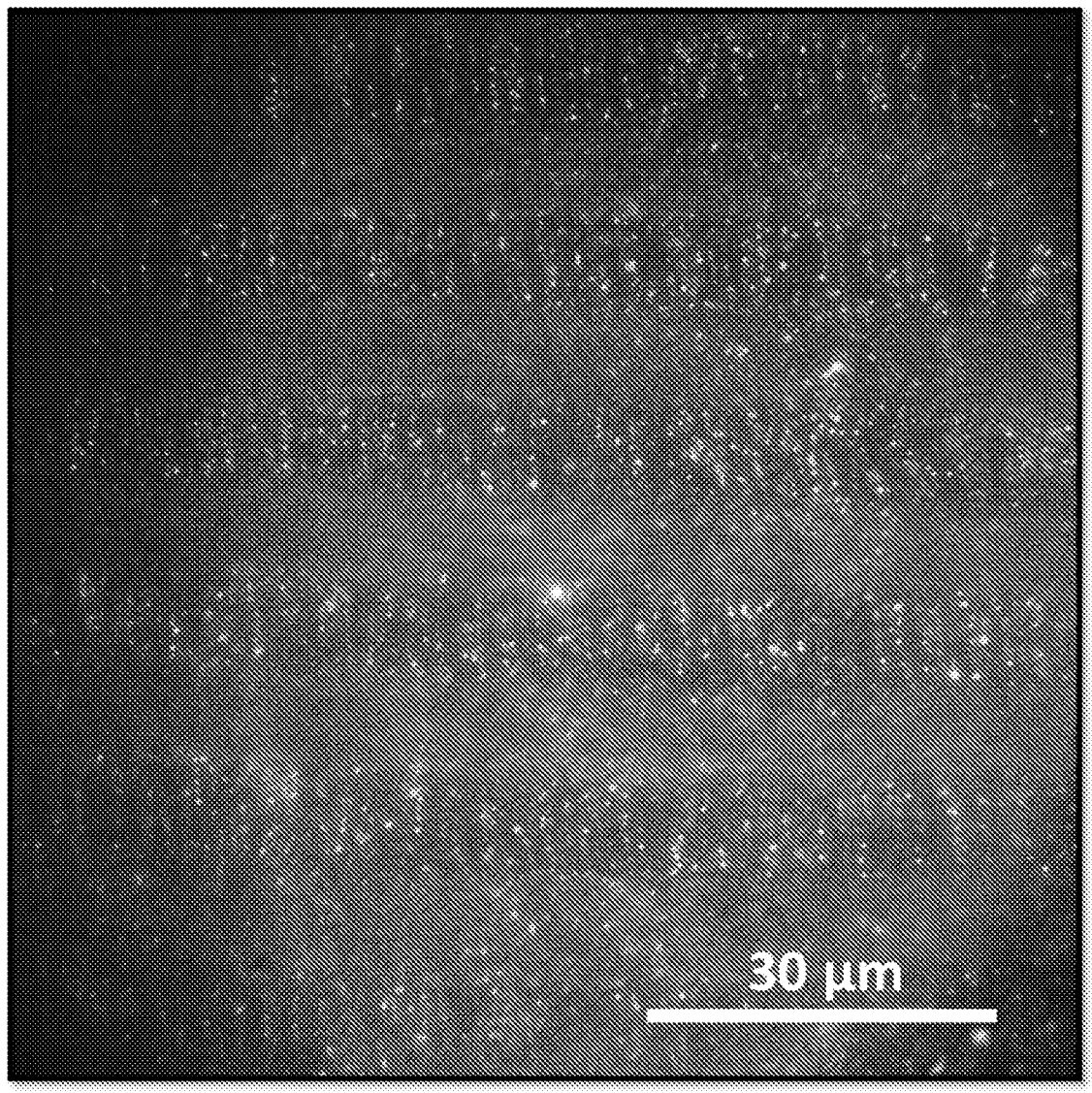
FIG. 13 shows that DNA molecules trapped in a hydrogel are extended with labeled reversible terminators using a DNA polymerase in a sequencing reaction. The labeled nucleotides appear as red, green and blue dots (or dots) across the surface features (bars).

In FIG. 13, fragments of genomic DNA can be trapped in a hydrogel. DNA may not be visible because it may not be stained. Random primers can be extended in the presence of a DNA polymerase using a mix of three reversibly terminated labeled nucleotides and one unlabeled nucleotide. The three labeled nucleotides can be rendered in three colors: red, green and blue (or shown as dots) in FIG. 13.

Many reactions, such as hybridization, protein binding and primers or nicks extension reactions, may be performed on captured DNA obtained by the methods disclosed herein.

Examples

Optical Sequencing of DNA Fragments Trapped in a Hydrogel Via the Incorporation of Reversibly Terminated Labeled Nucleotides.

DNA stretching is useful in all those applications where the molecule topology is relevant. DNA can be stretched across a surface with a variety of methods (e.g. meniscus retraction, flow fields, mechanical treading and others). However, once the molecule is stretched, surface effects may limit the ability of various enzymes or reagents to access and manipulate the DNA. A new method is disclosed herein to anchor DNA on intermittent capture bars or similar structures called surface features. The portions of DNA that are suspended between the surface features are more accessible to enzymatic reactions and other methods of manipulation than portions of DNA that are directly in contact with the surface (or surface features). For instance, this disclosed method can be used for DNA sequencing or DNA mapping. Moreover, it may offer a simple platform for protein-DNA binding assays.

Substrate Fabrication. Spin coat (at about 1000 rpm) the photoresist polymer SU-8 (2002 formulation) onto a 22×22 mm silicon substrate, obtaining a 1.75 μm thick layer of SU-8. Soft bake the coated substrate on a hotplate at about 95° C. for 1 minute. Put the substrate in vacuum in contact with a photomask that features an alternate pattern of 10 μm wide lines, separated by 10 μm. Expose the substrate to 80 mJ/cm$^2$ of UV light at 365 nm and finally post baked for 2 minutes at 95° C.

DNA Stretching. Anneal DNA to random primers after a heating step at 94° C. for 1 minute. Immerse the undeveloped substrate in a cuvette containing 50 ng of the annealed DNA suspended in 1.2 mL of MES buffer (pH 5.5). Incubate for 1 hour. The substrate is then retracted out of the cuvette at a speed of 67 μm/sec. The pulling direction has to be substantially perpendicular to the lines orientations in the pattern.

Substrate development. The substrate (with DNA stretched on top), is then developed in propylene glycol methyl ether acetate (PGMEA) for 1 minute. The portions of the polymer that have not been exposed to the UV light dissolve under the DNA, leaving the DNA suspended between the anchoring points as a "DNA bridge". The PGMEA in excess is removed by rinsing the substrate with isopropanol. Finally, the sample is rinsed with purified water. The surface is incubated in a solution of magnesium chloride and Tween 20 for 15 minutes.

Bind-silane coating of quartz substrates. 22×22 mm quartz slides are submerged in a solution containing ethanol, acetic acid and bind-silane (γ-methacryloxypropyltrimethoxysilane). The slides are agitated in the solution for 1 hour, and then rinsed with water and ethanol.

Acrylamide gel preparation. 6% acrylamide gel is mixed with t tetramethylethylenediamine (TEMED) and ammonium persulfate (APS) to start polymerization. 15 μL of the mixture are dispensed on the substrate and sealed with the quartz slide previously treated with bind-silane solution. After one hour the substrates are separated and the DNA, imbedded in gel, is transferred to the quartz slide. The gel is washed to remove excess of unpolymerized monomers.

First nucleotides incorporation. A solution containing a DNA polymerase, appropriate buffer, three reversible terminator labeled nucleotides and one reversible terminator but unlabeled nucleotide is applied on the sample and incubated for 20 minutes in an oven at 50° C. The substrate is washed with buffer to remove unincorporated nucleotides. DNA can be stained by applying a solution containing an intercalating dye (YOYO) to the sample surface, and then rinsed with water.

Imaging. The sample is imaged under a TIRF microscope in 4 different channels (3 for the labeled nucleotides and 1 for the DNA staining dye). Exposure time: 0.3 sec, camera gain: 300, laser power at the source: 100 mW.

Subsequent incorporations. A solution containing TCPE, a cleaving agent for the reversible terminators incorporated, is incubated on the sample surface for 15 minutes at 55° C., and then washed with water. A solution containing the DNA polymerase and the three reversible terminator labeled nucleotides and one reversible terminator but unlabeled nucleotide, is applied on the sample and incubated for 20 minutes in an oven at 50° C. Substrate is washed with buffer and then imaged. The last two steps are repeated for as many incorporations are desired While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of processing at least one nucleic acid molecule on a surface of a substrate, comprising:
   (a) stretching a nucleic acid molecule on a layer on a surface of a substrate; and
   (b) subsequent to (a), forming a plurality of discrete features from the layer on the surface of the substrate by removing a plurality of subsections from the layer on the surface of the substrate while the nucleic acid molecule is in contact with the layer;
   wherein, after (b), the nucleic acid molecule is in contact with at least two members of the plurality of discrete features, thereby suspending at least a portion of the nucleic acid between the at least two members of the plurality of discrete features.

2. The method of claim 1, wherein the plurality of discrete features form a topographical pattern.

3. The method of claim 1, further comprising:
   (c) subsequent to (b), forming a hydrogel on the surface of the substrate, the hydrogel being in contact with some or all members of the plurality of discrete features, wherein at least portions of the nucleic acid molecule are enclosed in the hydrogel.

4. The method of claim 3, further comprising:
   (d) subsequent to (c), removing the hydrogel from the surface of the substrate.

5. The method of claim 1, further comprising, in (a), stretching an additional nucleic acid molecule on the layer on the surface of the substrate.

6. The method of claim 5, wherein, after (b), the additional nucleic acid molecule is in contact with at least another two members of the plurality of discrete features, thereby suspending a portion of the additional nucleic acid molecule between the at least two members of the plurality of discrete features.

7. The method of claim 1, wherein each of the plurality of discrete features is independently a pit, a pore, a trough, a channel, a well, a pillar, a bump, a protrusion, a ridge, or a bar.

8. The method of claim 1, wherein each of the at least two members of the plurality of discrete features is independently a pillar, a bump, a protrusion, a ridge, or a bar.

9. The method of claim 1, wherein the nucleic acid molecule is a deoxyribonucleic acid (DNA), wherein the DNA is double-stranded or single-stranded.

10. The method of claim 1, further comprising: subsequent to (b) performing an enzymatic reaction on the nucleic acid molecule suspended between the at least two members of the plurality of discrete features.

11. The method of claim 1, further comprising: subsequent to (b), performing a protein binding reaction, a hybridization reaction, a primer-extension reaction catalyzed by a polymerase, a nicks translation reaction, or a nick extension reaction on the nucleic acid molecule suspended between the at least two members of the plurality of discrete features.

12. The method of claim 1, further comprising: before (a), applying a layer of a photoresist on top of the substrate.

13. The method of claim 12, further comprising: before (a), shining ultraviolet light through a mask onto the layer of the photoresist.

14. The method of claim 13, wherein the removing in (b) comprises developing the layer of the photoresist.

15. The method of claim 14, wherein each of the at least two members of the plurality of discrete features comprises the photoresist.

16. The method of claim 12, wherein the photoresist is a positive photoresist or a negative photoresist.

17. The method of claim 1, wherein before (a), the surface comprises a topographical pattern comprising the plurality of features and a plurality of cavities, wherein each of the plurality of features is independently a pillar, a bump, a protrusion, a ridge, or a bar; wherein each of the plurality of cavities is independently a pit, a pore, a trough, a channel, or a well; wherein the method further comprises: before (a), filling up each of the plurality of cavities with a photoresist.

18. The method of claim 17, wherein the removing in (b) comprises developing the layer of the photoresist, wherein the photoresist is a negative photoresist.

19. The method of claim 17, further comprising: before (a), shining ultraviolet light onto the photoresist on the surface, wherein the photoresist is a positive photoresist, wherein the removing in (b) comprises developing the layer of the positive photoresist.

20. A system comprising:
   (a) a substrate comprising a surface, the surface comprising a plurality of discrete features; and
   (b) a stretched nucleic acid molecule in contact with at least two members of the plurality of discrete features, wherein a portion of the stretched nucleic acid molecule is suspended between the at least two members of the plurality of discrete features, wherein each of the at least two members of the plurality of discrete features is independently a pillar, a bump, a protrusion, a ridge, or a bar,
   wherein the plurality of discrete features are formed by removing a plurality of subsections from a layer on the surface of the substrate while the stretched nucleic acid molecule is in contact with the layer.

* * * * *